(12) United States Patent
Mattern

(10) Patent No.: US 9,801,834 B2
(45) Date of Patent: Oct. 31, 2017

(54) CONTROLLED RELEASE DELIVERY SYSTEM FOR NASAL APPLICATION OF NEUROTRANSMITTERS

(71) Applicant: M et P Pharma AG, Emmetten (CH)

(72) Inventor: Claudia Mattern, Emmetten (CH)

(73) Assignee: M ET P PHARMA AG, Emmetten (CH)

( * ) Notice: Subject to any disclaimer, the term of this patent is extended or adjusted under 35 U.S.C. 154(b) by 0 days.

(21) Appl. No.: 14/881,332

(22) Filed: Oct. 13, 2015

(65) Prior Publication Data

US 2016/0089347 A1    Mar. 31, 2016

Related U.S. Application Data

(60) Division of application No. 13/194,926, filed on Jul. 30, 2011, now Pat. No. 9,186,320, which is a continuation of application No. 12/418,917, filed on Apr. 6, 2009, now abandoned, which is a continuation-in-part of application No. PCT/EP2007/008409, filed on Sep. 27, 2007.

(60) Provisional application No. 60/828,109, filed on Oct. 4, 2006.

(51) Int. Cl.
| | |
|---|---|
| *A01N 43/00* | (2006.01) |
| *A61K 31/33* | (2006.01) |
| *A61K 31/137* | (2006.01) |
| *A61K 9/00* | (2006.01) |
| *A61K 9/06* | (2006.01) |
| *A61K 9/127* | (2006.01) |
| *A61K 9/16* | (2006.01) |

(52) U.S. Cl.
CPC .......... *A61K 31/137* (2013.01); *A61K 9/0043* (2013.01); *A61K 9/06* (2013.01); *A61K 9/127* (2013.01); *A61K 9/1605* (2013.01)

(58) Field of Classification Search
USPC ......................................................... 514/183
See application file for complete search history.

(56) References Cited

U.S. PATENT DOCUMENTS

| | | | |
|---|---|---|---|
| 4,071,623 A | 1/1978 | Van Der Vies | |
| 4,083,973 A | 4/1978 | Van Der Vies | |
| 4,123,417 A | 10/1978 | Finberg | |
| RE29,892 E | 1/1979 | Bayne | |
| 4,315,925 A | 2/1982 | Hussain et al. | |
| 4,546,882 A | 10/1985 | Hsu et al. | |
| 4,581,225 A * | 4/1986 | Su .................. | A61K 9/0043 424/45 |
| 4,581,255 A | 4/1986 | Coggan et al. | |
| 4,752,425 A | 6/1988 | Martin et al. | |
| 4,786,678 A | 11/1988 | Dobreski et al. | |
| 4,812,448 A | 3/1989 | Knepper | |
| 4,826,852 A | 5/1989 | Haffner et al. | |
| 5,049,387 A | 9/1991 | Amkraut | |
| 5,397,771 A | 3/1995 | Bechgaard et al. | |
| 5,455,286 A | 10/1995 | Amidon et al. | |
| 5,500,261 A | 3/1996 | Takei et al. | |
| 5,514,673 A | 5/1996 | Heckenmuller et al. | |
| 5,624,960 A | 4/1997 | Wenzel et al. | |
| 5,635,203 A | 6/1997 | Gale et al. | |
| 5,645,856 A | 7/1997 | Lacy et al. | |
| 5,747,058 A | 5/1998 | Tipton et al. | |
| 5,756,071 A | 5/1998 | Mattern | |
| 5,863,554 A | 1/1999 | Illum | |
| 5,877,216 A | 3/1999 | Place et al. | |
| 5,891,920 A | 4/1999 | Hirano et al. | |
| 5,897,894 A | 4/1999 | Glass | |
| 6,187,323 B1 | 2/2001 | Aiache et al. | |
| 6,231,662 B1 | 5/2001 | Atkinson | |
| 6,248,363 B1 | 6/2001 | Patel et al. | |
| 6,287,588 B1 | 9/2001 | Shih et al. | |
| 6,310,089 B1 | 10/2001 | Watts et al. | |
| 6,319,905 B1 | 11/2001 | Mandel et al. | |
| 6,432,440 B1 | 8/2002 | Watts et al. | |
| 6,451,339 B2 | 9/2002 | Patel et al. | |
| 6,720,001 B2 | 4/2004 | Chen et al. | |
| 6,761,903 B2 | 7/2004 | Chen et al. | |
| 6,800,363 B2 | 10/2004 | Su et al. | |
| 6,815,506 B2 | 11/2004 | Takashima et al. | |
| 6,833,478 B2 * | 12/2004 | Bottaro .................. | A01N 25/02 424/617 |
| 6,838,091 B2 | 1/2005 | Lipari et al. | |
| 6,958,142 B2 | 10/2005 | Daniels et al. | |

(Continued)

FOREIGN PATENT DOCUMENTS

| | | |
|---|---|---|
| CA | 2135203 | 12/1993 |
| DE | 943792 | 6/1956 |

(Continued)

OTHER PUBLICATIONS

Dahlin et. al. (European Journal of Pharmaceutical Sciences (2001) 14:75-80).*
Masayoshi et. al. (Japan 01-160916, machine translated).*
Ikeda et. al. (Chem. Pharm. Bull. (1992) 40:2155-2158).*
Illum, "Transport of drugs from the nasal cavity to the central nervous system," European Journal of Pharmaceutical Sciences, vol. 11, pp. 1-18, 2000.
Dahlin et al., "Transfer of Dopamine in the Olfactory Pathway Following Nasal Administration in Mice," Pharmaceutical Research, vol. 17, No. 6, pp. 737-742, 2000.
Mathison et al., "Nasal Route for Direct Delivery of Solutes to the Central Nervous System: Fact or Fiction?," Journal of Drug Targeting, vol. 5, No. 6, pp. 415-441, 1998.
Kumar et al., "A New Approach to Fertility Regulation by Interfering with Neuroendocrine Pathways," Neuroendocrine Regulation of Fertility, Int. Symp., Simla, pp. 314-322, 1974.

(Continued)

*Primary Examiner* — Marcos Sznaidman
(74) *Attorney, Agent, or Firm* — Foley & Lardner LLP

(57) ABSTRACT

This invention relates to a galenical gel formulation for nasal administration of neurotransmitters/neuromodulators such as dopamine, serotonin or pregnenolone and progesterone. The special lipophilic or partly lipophilic system of the invention leads to high bioavailability of the active ingredient in plasma and brain caused by sustained serum levels and/or direct or partly direct transport from nose to the brain.

10 Claims, 2 Drawing Sheets

(56) References Cited

U.S. PATENT DOCUMENTS

| | | | |
|---|---|---|---|
| 7,186,706 | B2 | 3/2007 | Rosario-Jansen et al. |
| 8,574,622 | B2 | 11/2013 | Mattern |
| 8,609,043 | B2 | 12/2013 | Mattern |
| 8,784,869 | B2 | 7/2014 | Mattern |
| 8,784,882 | B2 | 7/2014 | Mattern |
| 8,877,230 | B2 | 11/2014 | Mattern |
| 9,186,320 | B2 | 11/2015 | Mattern |
| 2001/0055569 | A1 | 12/2001 | Davis et al. |
| 2002/0032171 | A1 | 3/2002 | Chen et al. |
| 2002/0114933 | A1 | 8/2002 | Gould |
| 2002/0136752 | A1 | 9/2002 | Whittle et al. |
| 2002/0198136 | A1 | 12/2002 | Mak et al. |
| 2004/0005275 | A1 | 1/2004 | Gizurarson et al. |
| 2004/0028613 | A1* | 2/2004 | Quay ............... A61K 45/06 424/45 |
| 2005/0100564 | A1* | 5/2005 | Mattern ............ A61K 31/568 424/400 |
| 2005/0153946 | A1 | 7/2005 | Hirsh et al. |
| 2005/0187188 | A1 | 8/2005 | Stein et al. |
| 2006/0140820 | A1 | 6/2006 | Mattern |
| 2006/0147385 | A1 | 7/2006 | Pike et al. |
| 2006/0210622 | A1 | 9/2006 | Pace et al. |
| 2006/0211664 | A1 | 9/2006 | Dudley |
| 2007/0134332 | A1* | 6/2007 | Turnell ............. A61K 9/1075 424/486 |
| 2007/0149454 | A1 | 6/2007 | Mattern |
| 2009/0227550 | A1 | 9/2009 | Mattern |
| 2010/0311707 | A1 | 12/2010 | Mattern |
| 2011/0009318 | A1 | 1/2011 | White et al. |
| 2011/0237562 | A1 | 9/2011 | Mattern |
| 2011/0245215 | A1 | 10/2011 | Carrara et al. |
| 2012/0005987 | A1 | 1/2012 | Mattern |
| 2012/0009250 | A1 | 1/2012 | Mattern |
| 2012/0058176 | A1 | 3/2012 | Mattern |
| 2012/0083480 | A1 | 4/2012 | Mattern |
| 2012/0277202 | A1 | 11/2012 | Mattern |
| 2012/0297730 | A1 | 11/2012 | Mattern |
| 2015/0005271 | A1 | 1/2015 | Mattern |

FOREIGN PATENT DOCUMENTS

| | | |
|---|---|---|
| DE | 1569286 | 10/1976 |
| EP | 0 160 501 | 11/1985 |
| EP | 0 349 091 | 1/1990 |
| GB | 1 569 286 | 6/1980 |
| GB | 2 237 510 | 5/1991 |
| JP | 0106716 | 1/1989 |
| JP | 01016716 | 1/1989 |
| JP | 2002-541111 | 12/2002 |
| JP | 2003/509453 | 3/2003 |
| JP | 2003-519085 | 6/2003 |
| TW | 175318 | 12/1991 |
| WO | WO 95/20945 A1 | 8/1995 |
| WO | WO 97/40823 | 11/1997 |
| WO | WO 98/47535 | 10/1998 |
| WO | WO 00/59512 | 10/2000 |
| WO | WO 01/41732 A1 | 6/2001 |
| WO | WO 01/95888 A1 | 12/2001 |
| WO | WO 02/051452 | 7/2002 |
| WO | WO 03/063833 A1 | 8/2003 |

OTHER PUBLICATIONS

Dahlin, "Nasal Administration of Compounds Active in the Central Nervous System—Exploring the Olfactory Pathway," Acta Universitatis Upsaliensis, Comprehensive Summaries of Uppsala Dissertations from the Faculty of Pharmacy 240, 48 pages, 2000.

Danner et al., "Androgen Substitution with Testosterone Containing Nasal Drops," vol. 3, pp. 429-435, 1980.

Jung et al., "Prolonged delivery of nicotine in rats via nasal administration of proliposomes," Journal of Controlled Release, vol. 66, pp. 73-79, 2000.

Ohman et al., "17β-Estradiol Levels in Blood and Cerebrospinal Fluid After Ocular and Nasal Administration in Women and Female Rhesus Monkeys (*Macaca mulatta*)," Contraception, vol. 22, No. 4, pp. 349-358, Oct. 1980.

Skipor et al., "Local transport of testosterone from the nasal mucosa to the carotid blood and the brain in the pig," Polish Veterinary Sciences, vol. 3, No. 1, pp. 19-22, 2000.

Hussain et al., "Intranasal Drug Delivery," Advanced Drug Delivery Reviews, vol. 29, pp. 39-49, 1998.

Kumar et al., "Pharmacokinetics of progesterone after its administration to ovariectomized rhesus monkeys by injection, infusion, or nasal spraying," Proc. Natl. Acad. Sci. USA, vol. 79, pp. 4185-4189, Jul. 1982.

David et al., "Bioavailability of progesterone enhanced by intranasal spraying," Experientia, vol. 37, pp. 533-534, 1981.

Wattanakumtornkul et al., "Intranasal hormone replacement therapy," Menopause: The Journal of The North American Menopause Society, vol. 10, No. 1, pp. 88-98, 2003.

Hussain et al., "Nasal Absorption of Propranolol from Different Dosage Forms by Rats and Dogs," Journal of Pharmaceutical Sciences, vol. 69, No. 12, pp. 1411-1413, Dec. 1980.

Patent Abstracts of Japan, Tanabe Seiyaku Co., Ltd., "Dopamine Nasal Administration Preparation," JP 01-160916, Jun. 23, 1989.

Mattern et al., "Development of a drug formulation for nasal administration of a testosterone precursor and test of its bioavailability," First World Congress on Aging Male, Geneva, Switzerland, 1998, Abstract.

Häcker et al., "Androgenic substitution for the ageing male by nasal administraton of a precursor of testosterone," First World Congress on Aging Male, Geneva, Switzerland, 1998, Abstract.

Müller et al., "Androgenic deficiencies of the ageing male and psychophysiological performance—test system for clinical diagnosis," First World Congress on Aging Male, Geneva, Switzerland, 1998, Abstract.

Nogueira et al., "In-Vivo monitoring of neostriatal dopamine activity after nasal drug administration in the rat: relevance to Parkinson's Disease and addiction," Neuroscience Meeting, San Diego, California, 1995, Abstract.

Topic et al., "Evidence for antidepressant-like action of intranasal application of testosterone," CINP Biennial International Congress, Munich, Germany, Jul. 13-17, 2008, Abstract.

Provasi et al., "Nasal delivery progesterone powder formulations comparison with oral administration," Bol. Chim. Farmaceutico, Anno 132—n. 10 poster, 1993.

Corbo et al., "Nasal delivery of progestational steroids in ovariectomized rabbits. II. Effect of penetrant hydrophilicity," International Journal of Pharmaceutics, vol. 50, pp. 253-260, 1989.

Cicnelli et al., "Nasally-administered progesterone: comparison of ointment and spray formulations," Maturitas, vol. 13, pp. 313-317, 1991.

Cicinelli et al., "Administration of unmodified progesterone by nasal spray in fertile women," Gynecol. Endocrinol., vol. 9, pp. 289-293, 1995.

Dondeti et al., "Bioadhesive and formulation parameter affecting nasal absorption", International Journal of Pharmaceutics, 127 (1996) 115-133.

Hussain et al., "Testosterone 17β-N, N-Dimethylglycinate Hydrochloride: A Prodrug with a Potential for Nasal Delivery of Testosterone", Journal of Pharmaceutical Sciences, vol. 91, No. 3, Mar. 2002, pp. 785-789.

Cicinelli et al., "Progesterone administration by nasal spray", Fertility and Sterility, vol. 56, No. 1, Jul. 1991, pp. 139-141.

Cicinelli et al., "Progesterone administration by nasal spray in menopausal women: comparison between two different spray formulations", Gynecol. Endocrinol., 6(1992), pp. 247-251.

Cicinelli et al., "Nasal spray administration of unmodified progesterone: evaluation of progesterone serum levels with three different radioimmunossay techniques", Maturitas Journal of the Climacteric & Postmenopause, 19(1994), pp. 43-52.

Steege et al., "Bioavailability of nasally administered progesterone", Fertility and Sterility, vol. 46, No. 4, 1986, pp. 727-729.

Viggiano et al., "Behavioural, pharmacological, morpho-functional molecular studies reveal a hyperfunctioning mesocortical dopamine system in an animal model of attention deficit and hypersctivity disorder," Neurosci. Biobehav. Rev. vol. 27, pp. 683-689, 2003.

(56) References Cited

OTHER PUBLICATIONS

Ikeda et al., "Enhancement of Bioavailablity of Dopamine via Nasal Route in Beagle Dogs," Chem. Pharm. Bull., vol. 40, No. 8, pp. 2155-2158, 1992.
Dahlin et al., "Levels of dopamine in blood and brain following nasal administration to rats," European Journal of Pharmaceutical Sciences, vol. 14, pp. 75-80, 2001.
Office Action dated Jun. 5, 2013 in U.S. Appl. No. 13/547,774 (US 2012/0277202).
Office Action dated Mar. 22, 2013 in U.S. Appl. No. 13/316,494 (US 2012/0083480).
Notice of Allowance dated Jul. 5, 2013 in U.S. Appl. No. 13/194,928 (US 2012/0009250).
Notice of Allowance dated Mar. 25, 2013 in U.S. Appl. No. 13/194,928 (US 2012/0009250).
Office Action dated Mar. 22, 2013 in U.S. Appl. No. 13/194,853 (US 2012/0058176).
International Search Report dated Mar. 31, 2005 in application No. PCT/EP2004/012122 (corresponding to US 2012/0083480).
European Search Report dated Apr. 6, 2004 in application No. EP 03 02 5769 (corresponding to US 2012/0083480).
Notice of Allowance dated Apr. 9, 2014 in U.S. Appl. No. 13/194,853 (now U.S. Pat. No. 8,784,882).
Notice of Allowance dated Mar. 19, 2014 in U.S. Appl. No. 13/547,774 (now U.S. Pat. No. 8,784,869).
Notice of Allowance dated Jul. 7, 2014 in U.S. Appl. No. 13/316,494 (now U.S. Pat. No. 8,877,230).
Office Action dated Jan. 13, 2012 in U.S. Appl. No. 12/796,165 (US 2010/0311707).
Office Action dated Nov. 16, 2009 in U.S. Appl. No. 11/560,187 (US 2007/0149454).
Office Action dated Mar. 18, 2009 in U.S. Appl. No. 11/560,187 (US 2007/0149454).
Office Action dated Oct. 29, 2008 in U.S. Appl. No. 11/560,187 (US 2007/0149454).
Office Action dated Aug. 20, 2008 in U.S. Appl. No. 11/560,187 (US 2007/0149454).
Office Action dated Feb. 5, 2008 in U.S. Appl. No. 11/560,187 (US 2007/0149454).
Office Action dated Sep. 14, 2007 in U.S. Appl. No. 11/560,187 (US 2007/0149454).
Office Action dated Jul. 8, 2010 in U.S. Appl. No. 10/772,964 (US 2005/0100564).
Office Action dated Sep. 29, 2009 in U.S. Appl. No. 10/772,964 (US 2005/0100564).
Office Action dated Jan. 15, 2009 in U.S. Appl. No. 10/772,964 (US 2005/0100564).
Office Action dated May 5, 2008 in U.S. Appl. No. 10/772,964 (US 2005/0100564).
Office Action dated Mar. 17, 2008 in U.S. Appl. No. 10/772,964 (US 2005/0100564).
Office Action dated Apr. 4, 2007 in U.S. Appl. No. 10/772,964 (US 2005/0100564).
Office Action dated Jul. 3, 2012 in U.S. Appl. No. 13/316,494 (US 2012/0083480).
Office Action dated Nov. 5, 2012 in U.S. Appl. No. 13/194,928 (US 2012/0009250).
Office Action dated Feb. 15, 2012 in U.S. Appl. No. 13/194,928 (US 2012/0009250).
Office Action dated Feb. 6, 2012 in U.S. Appl. No. 13/194,663 (US 2012/0005987).
International Search Report dated Dec. 21, 2007 in application No. PCT/EP2007/008409.
Mattern et al., "Testosterone supplementation for hypogonadal men by the nasal route," The Aging Male, vol. 11, No. 4, pp. 171-178, Dec. 2008.
Banks et al., "Delivery of testosterone to the brain by intranasal administration: Comparison to intravenous testosterone," Journal of Drug Targeting, vol. 17, No. 2, pp. 1-7, Dec. 16, 2008.
Ko et al., "Emulsion formulations of testosterone for nasal administrations," J. Microencapsulation, vol. 15, No. 2, pp. 197-205, 1998.
Office Action dated Jan. 6, 2011 in U.S. Appl. No. 12/418,917 (US 2009/0227550).
Office Action dated Mar. 8, 2011 in U.S. Appl. No. 12/418,917 (US 2009/0227550).
Notice of Allowance dated Sep. 22, 2015 in U.S. Appl. No. 14/322,319 (US 2015/0005271).
Office Action dated May 22, 2015 in U.S. Appl. No. 14/322,319 (US 2015/0005271).
Buddenberg, et al. *Behavioral actions of intranasal application of dopamine: effects on forced swimming, elevated plus-maze and open field parameters.* (Neuropsychobiology. 2008;57(1-2):70-9).
De Souza Silva, et al. *Increased Neostriatal Dopamine Activity After Intraperitoneal or Intrana.sal Administration of L-DOPA: On the Role of Benserazide Pretreatment.* (Synapse. 1997 27:294-302.
De Souza Silva, et al. *Intranasal administration of the dopaminergic agonists L-DOPA, amphetamine, and cocaine increases dopamine activity in the neostriatum: a microdialysis study in the rat*, (I Neurochem. Jan. 1997;68(1):233-9).
De Souza Silva, et al. *Intranasal Dopamine Application Increases Dopatninergic Activity in the Neostriatum and Nucleus Accumbens and Enhances Motor Activity in the Open Field.* (Synapse. Mar. 2008;62(3):176-84).
Tavares, et al. *Effects of intra-nasally administered testosterone on sexual proceptive behavior in female capuchin monkeys (Cebus apella).* (Behav Brain Res. Apr. 16, 2007;179(1):33-42).
Topic, et al. *Prolonged effects of intra-nasally administered testosterone on sexual proceptive behavior in female capuchin monkeys (Cebus apella).* (Behav Brain Res. Apr. 16, 2007;179(1):60-68).
Taiwanese Search Report dated Jan. 2006 in application No. 093129982.
Notice of Allowance dated Oct. 20, 2016 in U.S. Appl. No. 14/965,137 (US 2016-0136090).
U.S. Appl. No. 15/612,454, filed Jun. 2, 2017, Claudia Mattern.

\* cited by examiner

US 9,801,834 B2

CONTROLLED RELEASE DELIVERY SYSTEM FOR NASAL APPLICATION OF NEUROTRANSMITTERS

INCORPORATION BY REFERENCE

This application is a divisional of U.S. patent application Ser. No. 13/194,926, filed Jul. 30, 2011, which is a continuation of U.S. patent application Ser. No. 12/418,917, filed Apr. 6, 2009, which is a continuation-in-part application of International Patent Application Serial No. PCT/EP2007/008409 filed Sep. 27, 2007, which published as PCT Publication No. WO/2008/040488 on Apr. 10, 2008, which claims the benefit of U.S. Provisional Application No. 60/828,109 filed Oct. 4, 2006.

The foregoing application, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The invention generally relates to a formulation used for the controlled release and delivery of neurotransmitters and neuromodulator agents to the systemic circulation and/or to brain tissue via administration to the nasal cavity.

BACKGROUND OF THE INVENTION

A growing body of evidence suggests that brain-acting compounds, such as neurosteroids (e.g., androgens, progestins) or neurotransmitters (e.g., dopamine, derived from 3,4-dihydroxyphenylalanine (L-DOPA, or levodopa), serotonin, epinephrin, norepinephrine), have a modulatory role in the regulation of disorders influenced by receptors in the brain, such as depression, Parkinson's disease, Alzheimer's, psychiatric disorders and even loss of libido and aggression.

Neurosteroids act as modulators, either as stimulators or inhibitors, of several neurotransmitters. Neurotransmitters are chemicals that relay, amplify and modulate electrical signals between a neuron and another cell. Some neurotransmitters are excitatory, while others are primarily inhibitory. In many cases, as with dopamine, it is the function of the receptor which determines whether the transmitter is excitatory or inhibitory.

The brain floats in about 150 ml of cerebrospinal fluid (CSF), which slowly circulates down through the four ventricles, up through the subarachnoid space and exits into the cerebral veins through the arachnoid vili. Since the brain has no lymphatic system, the CSF serves as a partial substitute. While the brain and CSF are separated by the somewhat permeable pia mater, the blood-cerebrospinal fluid barrier and the blood-brain barrier (BBB) represent substantial protection against undesirable blood substances.

The BBB creates a protected chemical environment wherein certain molecules are able to perform functions independent of the functions those molecules may perform elsewhere in the body. One example of such a molecule is the neurotransmitter dopamine. When applied as an infusion, dopamine may be used for the treatment of heart attacks or kidney failure, but this mode of administration of dopamine is not suitable for the treatment of neurological disorders, such as Parkinson's disease.

L-DOPA is typically used to increase dopamine levels in the brain for the treatment of Parkinson's disease and Dopa-Responsive deficiencies because it is able to cross the blood-brain barrier, whereas dopamine itself cannot. Once L-DOPA has entered the central nervous system (CNS), it is metabolized to dopamine by aromatic L-amino acid decarboxylase.

Often, during treatment of neurological diseases such as Parkinson's Disease, L-DOPA is administered to patients together with other compounds, including carbidopa, benserazide, and Entacapone/tolcapone. Further, other drugs or complimentary therapies may be administered to Parkinson's patients in concert with L-DOPA treatment, including dopamine agonists, MAO-B inhibitors, glial-derived neurotropic factor for gene therapy, and several neuroprotective agents.

To increase the efficacy of medicinal treatments of CNS disorders, delivery of molecules to the brain via delivery to the nasal cavity has been investigated. The inventors have recently provided evidence in Banks, et al. (J Drug Target. 2009 February; 17(2):91-7), incorporated herein by reference, that intranasal administration of testosterone is able to target the brain, and in particular, is able to target the olfactory bulb, hypothalamus, striatum, and hippocampus. Drug delivery to the brain via the nasal cavity potentially offers many advantages that include direct access to the brain, rapid adsorption into the nasal mucosa due to the abundant presence of capillary vessels in the nose, rapid onset of action, avoidance of hepatic first-pass metabolism, utility for chronic medication, and ease of administration. However, still little is known on factors controlling the nasal delivery of drugs to the brain. A drug can reach the brain by different ways, including olfactory neuronal pathway, extraneuronal olfactory epithelial pathway, trigeminal nerve pathway, systemic pathway. It is also possible that more of the aforementioned pathways may contribute to the delivery of the molecule to the brain. Once a drug is in the brain, it's amount can be further influenced by BBB efflux transporter systems.

Thus, there has been a long-felt need in the art for investigations into and the generation of formulations that facilitate molecular uptake into the tissue of the nasal cavity, thereby increasing the concentration of the drug in brain tissue.

However, maintaining clinically effective drug concentrations in vivo, particularly in brain tissue, has been a challenge. The time period during which molecules may become absorbed is reduced as a result of the rapid mucociliary clearance of a therapeutic agent from the site of deposition and the presence of enzymes in the nasal cavity, which that may cause degradation of the therapeutic agent.

Many efforts have been made in the art in attempt to overcome these limitations.

GB 1987000012176 relates to the use of bioadhesive microspheres to increase the length of time that molecules reside in the nasal cavity. It has also been found that the use of enhancers and stabilizers improves permeability of the nasal membrane and prevents drug degradation, respectively. PCT/GB98/01147 (U.S. Pat. No. 6,432,440) pertains to the use of in situ gelling pectin formulations for drug delivery.

Bayne, U.S. Reissue Pat. No. RE29,892 pertains to a method of increasing the dopamine concentration in brain tissue through administration of a composition comprising dopamine and a hydrazine compound. The method allows for administration of the composition topically, rectally, orally, or parenterally. Preferred compositions include hydrazine compounds such as L-α-hydrazino-α-lower alkyl-3,4-dihydroxyphenyl propionic acid and L-DOPA and its pharmaceutically accepted salts.

Haffner et al., U.S. Pat. No. 4,826,852, relates to the treatment of psychoses such as schizophrenia and discloses methods of administrating ergolinyl compounds to increase dopamine concentrations in mammalian brain tissue.

Additionally, Wenzel et al., U.S. Pat. No. 5,624,960, pertains to the treatment of Parkinson's disease through the oral administration of a composition containing levodopa and carbidopa (MK-486). Further, Mandel et al., U.S. Pat. No. 6,319,905, relates to the tightly modulated production of L-DOPA in the mammalian brain by gene therapy. In Mendel et al., modulators such as tetrahydropterin (PH4) are used to control the generation of dopamine.

Despite the latter attempts to develop an effective nasal delivery system, there remains a need in the art to identify a formulation that, inter alia, limits the rate of mucociliary clearance and degradation of molecules in the nasal cavity, thereby increasing the brain's availability to such molecules, particularly neurotransmitters. Preferably, the formulation should have physical and chemical properties that facilitates brain uptake of molecules/drugs, such as dopamine. The identification of a formulation that may increase the bioavailability of neurotransmitters to brain tissue would provide much-needed treatment options for diseases associated with, for example, dopamine or serotonin deficiency in the brain, including depression, Parkinson's disease, attention deficit hyperactivity disorder (ADHD), addiction to drugs and alcohol, and various psychiatric disorders.

Citation or identification of any document in this application is not an admission that such document is available as prior art to the present invention.

SUMMARY OF THE INVENTION

The presently claimed invention demonstrates that the incorporation of various neurotransmitter agents into a unique lipophilic or partly lipophilic formulation, which when delivered to the nasal cavity, results in clinically effective sustained serum levels in plasma and CSF. These levels in turn increase the bioavailability of drugs to the systemic circulation and to brain tissue.

The presently claimed invention comprises a formulation for nasal application comprising: (a) at least one active ingredient selected from the groups consisting of a neurotransmitter and a neuromodulator agent; (b) at least one lipophilic or partly lipophilic carrier; and (c) a compound or a mixture of compounds having surface tension decreasing activity, an amount effective for generation of contact of the formulation with a hydrophilic mucous membrane and optionally (d) a viscosity-regulating agent. The formulation may also contain minor proportions of one or more compounds including but not limited to absorption promoters, substances that inhibit enzymatic degradation or efflux, preservatives, flavors and antioxidants.

In one embodiment of the invention, the at least one active ingredient is a neurotransmitter. In a preferred embodiment, the neurotransmitter may be dopamine, serotonin, epinephrine or norepinephrine.

In another embodiment, the at least one active ingredient is a neurotransmitter or neuromodulator agent(s).

In yet another embodiment, the formulation may comprise more than one neurotransmitter and/or neuromodulator agent. In a preferred embodiment, the formulation may comprise dopamine or L-DOPA and their derivatives.

In one embodiment, the active ingredient(s) may comprise 0.01 to 6% by weight, preferably 0.1 to 4% by weight, more preferably 0.5 to 2% by weight, and most preferably at around 2% by weight of the formulation.

In one embodiment of the invention, the lipophilic carrier may comprise oil, fats and/or other lipids. Lipids may be any lipophilic molecules, including but not limited to fats, oils, waxes, cholesterol, sterols, monoglycerides, diglycerides, phospholipids.

In a preferred embodiment, the oil is a vegetable oil. Most preferably, the oil is caster oil.

In yet another preferred embodiment, the oil may between 30% and 98% by weight, preferably between 60 and 98% by weight, more preferably between 75% and 95% by weight, even more preferably between 85% and 95% by weight and most preferably around 90% by weight of the formulation.

In a further embodiment, component (c) may comprise at least one surfactant selected from the group consisting of lecithin, fatty acid ester of polyvalent alcohols, of sorbitanes, of polyoxyethylensorbitans, of polyoxyethylene, of sucrose, of polyglycerol and/or at least one humectant selected from the group consisting of sorbitol, glycerine, polyethylene glycol, and macrogol glycerol fatty acid ester, or a mixture thereof. In a preferred embodiment, component (c) may comprise an oleoyl macrogolglyceride or a mixture of oleoyl macrogolglycerides.

In a preferred embodiment, component (c) may comprise 1 to 20% by weight, preferably 1 to 10% by weight, more preferably 1 to 5% by weight, and most preferably at around 4% by weight of the formulation.

In another embodiment, the viscosity-regulating agent may comprise a thickener or gelling agent selected from the group consisting of cellulose and cellulose derivatives, polysaccharides, carbomers, polyvinyl alcohol, povidone, colloidal silicon dioxide, cetyl alcohols, stearic acid, beeswax, petrolatum, triglycerides and lanolin, or a mixture thereof. More preferably, the viscosity-regulating agent is colloidal silicon dioxide.

In a preferred embodiment, the viscosity-regulating agent may comprise 0.5 to 10% by weight, preferably 0.5 to 5% by weight, more preferably 2 to 5% by weight, and most preferably at around 4% by weight of the formulation.

While not wishing to be bound by theory, it is believed that nasal administration of the galenical gel formulation of the presently claimed invention may be able to facilitate selective recruitment of molecules to brain tissue by providing access directly to the brain, which in turn may provide for new clinical applications, for example, the use of neurotransmitters to treat CNS disorders.

Accordingly, it is an object of the invention to not encompass within the invention any previously known product, process of making the product, or method of using the product such that Applicant reserves the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicant reserves the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION

Figure 1:
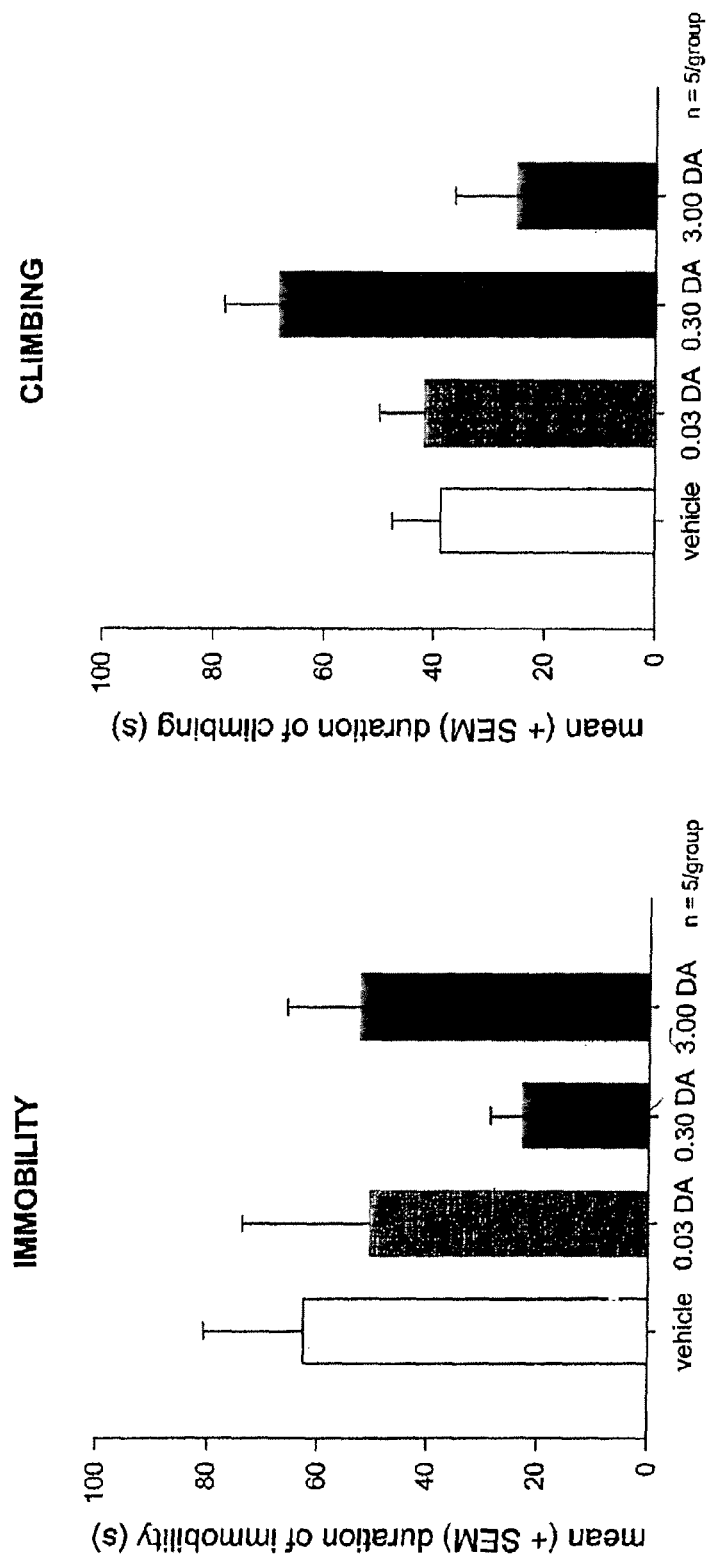
FIG. 1 shows the effect of nasal dopamine gel on immobility and climbing of depressed rats.

The galenical gel formulation of the presently claimed invention is chemically and physically stable and can be in the form of a suspension or a solution of the pharmacologically active substance. In a preferred embodiment, the galenical gel formulation of the invention is filled into a preservative-free device able to accurately deliver doses of the above formulation, even at a high viscosity.

After nasal application of the galenical gel formulation, the active ingredient or active ingredient particles are typically efficiently trapped at the deposition site and are typically absorbed at a predictable rate across the mucous membrane of the patient, thereby limiting possible deactivation by metabolizing enzymes and/or protein-binding.

It is also understood that the terms and expressions used herein have the ordinary meaning as is accorded to such terms and expressions with respect to their corresponding respective areas of inquiry and study except where specific meanings have otherwise been set forth herein.

The term "higher availability" or "higher bioavailability" shall mean that after application of the active ingredient(s), significant and constant in vivo therapeutic drug concentrations, especially in the brain, are maintained for an extended period of time.

The composition of the invention may comprise a neurotransmitter and/or neuromodulator agent. A neurotransmitter, as used herein, may be a molecule used for signaling between nerve cells or neurons. Neurotransmitter molecules typically pass between neurons at synapses, and may causes a rapid, short-lived and dramatic response. Neurotransmitters may degrade rapidly, resulting in restoration of the resting membrane potential. Examples include but are not limited to Acetylcholine, Monoamines (epinephrine, norepinephrine, dopamine, serotonin, melatonin, histamine), Amino acids (glutamate, gamma aminobutyric acid (GABA), aspartate, glycine), Purines (Adenosine, ATP, GTP, and their derivatives), neuroactive peptides (Substance P. N-Acetylaspartylglutamate), Neurohypophyseal transmitters (Oxytocin, Vasopressin), Opioids (Endorphin), zinc, nitric oxide, carbon monoxide, and chemical modifications of such molecules, such as esters.

Neurotransmitters such as dopamine, serotonin, epinephrine and norepinephrine contain the catechol moiety typically synthesized from the amino acid tyrosine.

One neurotransmitter commonly associated with any number of responses is dopamine or 4-(2-aminoethyl)-1,2-benzenediol. Dopamine is commonly regarded as an endogenous catecholamine with α and β adrenergic activity.

L-DOPA is commonly synthesized from aminotyramine and converted into dopamine in the brain. Other neurotransmitters are typically contained in synaptic vesicles in terminals of the presynaptic neuron, and upon stimulation of an action potential, are released into the synaptic cleft to induce a response in the post synaptic cell. Iontophoresis of the neurotransmitter into a synaptic cleft induces the same postsynaptic response. The neurotransmitter then degrades rapidly resulting in restoration of the resting potential.

Other catecholamines known to have various utilities include epinephrine, norepinephrine, and serotonin.

A neuromodulator agent, as used herein, may be a substance other than a neurotransmitter, released by a neuron at a synapse and conveying information to adjacent or distant neurons, either enhancing or dampening their activities. Neuromodulation is the process in which several classes of neurotransmitters in the nervous system regulate diverse populations of neurons. Neuromodulators may act not only on the input system but may change the transformation itself to produce the proper contractions of muscles as output. Neuromodulator agents may also include neurosteroids. A variety of steroids are synthesized in the central and peripheral nervous system, especially in myelinating glial cells, from cholesterol or steroidal precursors imported from peripheral sources. Such steroids are defined as neurosteroids. Neurosteroids may rapidly alter neuronal excitability through interaction with neurotransmitter-gated ion channels. In addition, neurosteroids may also exert effects on gene expression via intracellular steroid hormone receptors. Examples include but are not limited to pregnenolone, dehydroepiandrosterone, their sulfates, and reduced metabolites such as the tetrahydroderivative of progesterone 3α-hydroxy-5α-pregnane-20-one. Neuromodulator agents also include chemical modifications of neurosteroids, such as esters and synthetic neurosteroids such as minaxolone, ganaxolone.

In a preferred embodiment, the active ingredient may comprise 0.01 to 6% by weight, preferably 0.1 to 4% by weight, more preferably 0.5 to 2% by weight, and most preferably at around 2% by weight of the formulation.

The carrier of the invention functions to dissolve or suspend the drug and otherwise support the various constituents of the invention. To that end, the carrier has a lipophilic nature or character. Suitable families of oils include fatty acids and oils such as mineral and vegetable oils, in particular, fatty acids and oils derived from vegetable stock are especially useful. Both linear and branched chain acids and oils are useful including those oils and acids with various levels of saturation and substitution. Chain size including but is not limited to formic, acetic, propionic, butyric, valeric, caproic, emanthic, caprylic, pelargonic, capric, laurie, myristic, palmitic and stearic, among others, all represent useful oil and acid moieties.

The term "lipophilic carrier" may comprise, but is not limited to, fats and/or vegetable oil such as castor oil, soybean oil, sesame oil, or peanut oil, fatty acid esters such as ethyl- and oleyloleat, isopropylmyristate, medium chain triglycerides, glycerol esters of fatty acids, or polyethylene glycol, phospholipids, white soft paraffin, or hydrogenated castor oil, or a mixture thereof. In one embodiment, the active ingredient may also be incorporated into an oil mixture. In a preferred embodiment, the vegetable oil is castor oil.

The particular amount of lipophilic carrier that constitutes an effective amount is dependent on the particular viscosity regulating agent used in the formulation. It is therefore not practical to enumerate specific amounts for use with specific formulations of the invention.

In a preferred embodiment, the lipophilic carrier may comprise between 30% and 98% by weight, preferably between 60 and 98% by weight, more preferably between 75% and 95% by weight, even more preferably between 85% and 95% by weight, and most preferably around 90% by weight of the formulation.

The surface active agent or surfactant of the invention functions to decrease surface tension in the composition of the invention. Surfactants are generally regarded as those compositions which have both hydrophilic and lypophilic character. The lypophilic character of the surfactant typically takes the form of a pendent moiety having little if any charge. In turn, the hydrophilic character of the surfactant is typically charged and dictates the class into which the surfactant is identified. For example, surfactants typically used in the invention include nonionic surfactants, anionic surfactants, amphoteric surfactants, and cationic surfactants.

In one embodiment, component (c), a compound or a mixture of compounds having surface tension decreasing activity, may comprise at least a surfactant including, but not limited to, lecithin, fatty acid ester of polyvalent alcohols, fatty acid ester of sorbitanes, fatty acid ester of polyoxyethylensorbitans, fatty acid ester of polyoxyethylene, fatty acid ester of sucrose, fatty acid ester of polyglycerol, and/or at least one humectant such as sorbitol, glycerine, polyethylene glycol, or macrogol glycerol fatty acid ester. Particularly useful, however, are oleoyl macrogolglycerides (such as LABRAFIL® 1944 CS, as available from Gattefosse (Saint-Priest, France)).

As defined herein, "surface tension decreasing activity" shall mean having a surface tension that results in generating contact of the formulation to the hydrophilic mucous membranes of the nasal cavity.

In one embodiment, the active ingredient/neurotransmitter may be incorporated into a surfactant mixture. The particular amount of surfactant that constitutes an effective amount is dependent on the particular oil or oil mixture used in the formulation. It is therefore not practical to enumerate specific amounts for use with specific formulations of the invention. Typically, however, the surfactant may comprise 1 to 20% by weight, preferably 1 to 10% by weight, more preferably 1 to 5% by weight, and most preferably at around 4% by weight of the formulation.

The term "viscosity-regulating agent" shall mean a thickener or gelling agent.

Examples of a viscosity-regulating agent include, but are not limited to, cellulose and derivatives thereof, polysaccharides, carbomers, polyvinyl alcohol, povidone, colloidal silicon dioxide, cetyl alcohols, stearic acid, beeswax, petrolatum, triglycerides, lanolin, or the like. A preferred viscosity regulating agent is colloidal silicon dioxide (such as AEROSILO®, as available from Degussa).

The incorporation of the active ingredient is also possible into a mixture of thickeners or gelling agents. The particular amount of thickener/gelling agent that constitutes an effective amount is dependent on the particular oil or oil mixture used in the formulation. It is therefore not practical to enumerate specific amounts for use with specific formulations of the invention. Typically, however, the thickener/gelling agent(s) may comprise 0.5 to 10% by weight, preferably 0.5 to 5% by weight, more preferably 2 to 5% by weight, and most preferably at around 4% by weight of the formulation.

Preferred weight percentages for components of the galenical gel formulation are shown in Table 1.

TABLE 1

Preferred weight percentages components of the galenical gel formulation
Wt-%

|  | Useful | Preferred | More Preferred |
|---|---|---|---|
| Active Ingredient (e.g. Neurotransmitter/ Neuromodulator agent | 0.01 to 6 | 2 to 4 | 0.5 to 2 |
| Lipophilic Carrier | 30 to 98 | 60 to 98 | 85 to 95 |
| Surfactant | 1 to 20 | 1 to 10 | 1 to 5 |
| Viscosity Regulating Agent | 0.5 to 10 | 0.5 to 5 | 2 to 5 |

Generally, the galenical formulation of the invention can be prepared easily by the following conventional method:

The lipophilic carrier and surfactant are filled into a stirrer vessel and about 75% of the viscosity regulating agent is mixed in. The active ingredient is added while stirring to obtain a homogenous dispersion of the active ingredient. Next, the formulation is adjusted to the necessary viscosity with the remainder of the viscosity regulating agent.

In a preferred embodiment, the formulation may be filled into a preservative-free container.

Because the active ingredient, particularly a neurotransmitter, may have lower levels of solubility in water, release from the formulation is the rate-limiting step for adsorption. The presently claimed invention demonstrates that the incorporation of the active ingredient into an oily formulation containing a suitable surfactant leads to physiologically clinically effective serum and brain levels and to an appropriate sustained action of the active ingredient over time.

This sustained and clinically favorable release of the active ingredient is due to the interaction of the compounds in the oily carrier, which remains on the mucous membrane of the nasal cavity for a prolonged duration of time.

The active ingredient of this invention may be introduced into the formulation also in a processed form, such as microspheres, liposomes, among others.

The formulation according to this invention may also be processed into powder form, such as by lyophilization or spray-drying.

The most preferred formulation of the presently claimed invention is presented in Table 2.

TABLE 2

Most Preferred formulation

| Compound | Amount per container | Delivery per spray |
|---|---|---|
| Dopamine/L-DOPA | 2% | ~2.8 mg |
| Colloidal silicon dioxide | 4% | ~4.2 mg |
| Oleoyl macrogol-glycerides | 4% | ~5.6 mg |
| Castor Oil | 90% | ~127.4 mg |

In one embodiment, the formulation is administered to a patient. In a preferred embodiment, the formulation is administered to a human.

When administered to a patient, the formulation that optionally comprises a pharmaceutically acceptable vehicle may be administered by absorption through mucocutaneous linings and may be administered together with another biologically active agent. Administration may be local.

In a specific embodiment, the term "pharmaceutically acceptable" means approved by a regulatory agency of the Federal or a state government or listed in the U.S. Pharmacopeia or other generally recognized pharmacopeia or otherwise proven as safe for use in animals, mammals, and more particularly in humans. The term "vehicle" refers to a diluent, adjuvant, excipient, or carrier with which a compound of the invention is administered. Such pharmaceutical vehicles can be lipophilic semisolids or liquids such as oils, including those of petroleum, animal, vegetable or synthetic origin, such as peanut oil, soybean oil, mineral oil, sesame oil and the like.

The amount of the formulation that will be effective in the treatment of a particular disease will depend on the nature of the disease, and can be determined by standard clinical techniques. In addition, in vitro or in vivo assays may optionally be employed to help identify optimal dosage ranges. The precise dose to be employed will also depend on the seriousness of the disease, and should be decided according to the judgment of the practitioner and each patient's circumstances.

Recommended dosages for administration by inhalation are in the range of about 0.001 milligram to about 200 milligrams per kilogram of body weight per day. Effective doses may be extrapolated from dose-response curves derived from in vitro or animal model test systems. Such animal models and systems are well known in the art.

The formulation is preferably assayed in vitro and in vivo, for the desired therapeutic or prophylactic activity, prior to use in humans. Animal model systems can be used to demonstrate safety and efficacy.

EXAMPLES

The invention will now be further described by way of the following non-limiting examples.

Example 1

Nasal Administration of Dopamine to Rats

Figure 2:
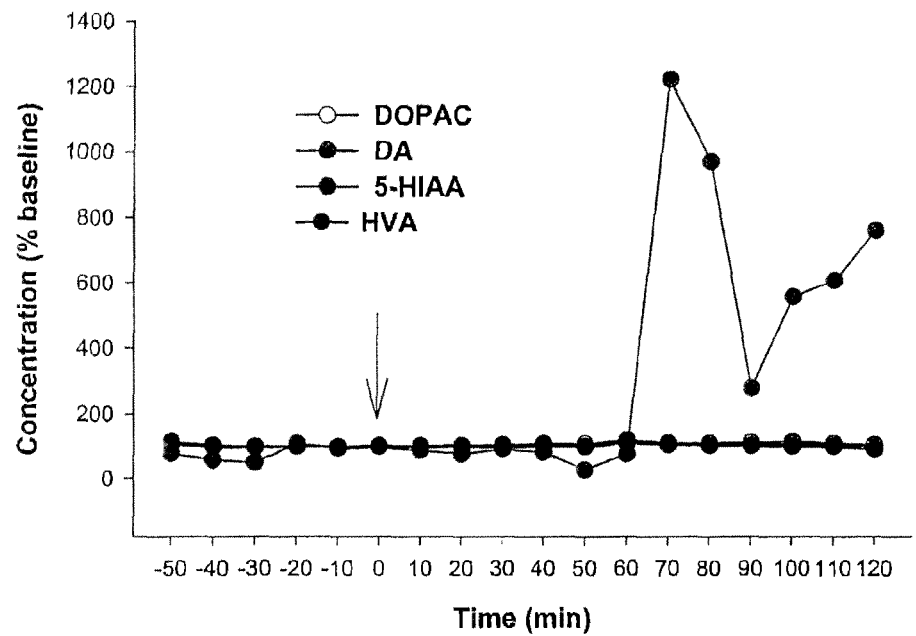
FIG. 2 shows the concentration of dopamine and metabolites in nucleus accumbens and neostriatum after nasal administration of dopamine.
Figure 2:
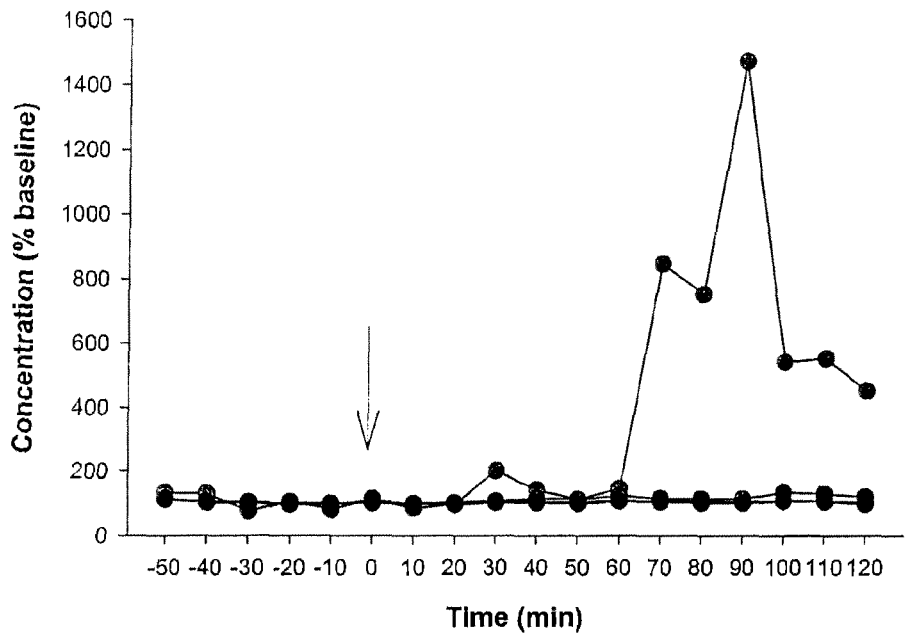

A dopamine (DA) gel of the inventive formulation was nasally administered to rats used in the validated "forced swimming test." As shown in FIG. 1, the administration of dopamine results in anti-depressive-like effects. As shown in FIG. 2, strong dopaminergic activity in the neostriatum and ventral striatum (nucleus accumbens) was observed after nasal application of dopamine with the inventive formulation.

Generally, antidepressants must be administered for an extended length of time before antidepressive effects are observed. Surprisingly, after nasal application to rat of the dopamine gel formulation, antidepressive effects occurred within hours and without any observable side effects, such as those side effects known to occur with desipramine (apathy) or fluoxetine (weight loss).

After nasal application to rats of dopamine in the inventive gel formulation, the concentration of dopamine in the nucleus accumbens and neostriatum level increased rapidly by more than 1000 percent. These results differ from those previously described. After nasal application of an aqueous dopamine solution to mice, Bjorn Jansson, Comprehensive Summaries of Uppsala Dissertations from the Faculty of Pharmacy 305 (2004), found dopamine in the olfactory bulb but the compound peaked after four hours. After nasal application to rats of aqueous dopamine solution, Maria Dahlin, Comprehensive Summaries of Uppsala Dissertations from the Faculty of Pharmacy 240 (2000), found dopamine in CSF after a short time but the increase of the compound from baseline was much lower than with the nasal gel of the invention. Ikeda et al., Chem. Pharm. Bull. 40(8): 2155-2158 (1992), increased bioavailability of nasally-given dopamine by some degree using the excipients hydroxypropyl cellulose (HPC) and Azone (1-dodecylazacycloheptan-2-one), respectively. De Souza Silva et al., Synapse 27:294-302 (1997), showed that by nasally applying to rats an aqueous L-DOPA methyl ester solution (50 mg/kg), the dopamine level in the neostriatum were increased by about 130%. The metabolites 3,4-dihydroxyphenyl acetic acid (DOPAC) and homovanillic acid (HVA) slightly increased by contrast to what was seen after intraperitoneal (IP) application of L-DOPA methyl ester in De Souza Silva et al., J. Neurochem. 68(1): 233-239 (1997).

Furthermore, the metabolism of dopamine appears to be quite different than that previously described. Unexpectedly, as shown in FIG. 2, dopamine in the CSF was not metabolized to 3,4-dihydroxyphenyl acetic acid (DOPAC) or homovanillic acid (HVA) as is typically seen. These results demonstrate that nasal application of dopamine in the inventive gel formulation may be useful for the treatment of diseases associated with dopamine deficiency in the brain, such as Parkinson's disease, attention deficit hyperactivity disorder (ADHD), and addiction to drugs and/or alcohol.

The features disclosed in the foregoing description, in the claims and/or in the drawings may, both separately and in any combination thereof, be material for realizing the invention in diverse forms thereof.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A dopamine gel formulation for nasal administration comprising:
   (a) dopamine in an amount of from about 0.01% to about 6% by weight of the dopamine gel formulation;
   (b) castor oil in an amount of from 75% to 95% by weight of the dopamine gel formulation;
   (c) oleoyl macrogolglyceride or a mixture of oleoyl macrogolglycerides in an amount of from 0.5% to about 20% by weight of the dopamine gel formulation; and
   (d) colloidal silicon dioxide in an amount of from 0.5% to 10% by weight of the dopamine gel formulation.

2. The dopamine gel formulation according to claim 1, wherein said dopamine is present in an amount of from 0.5% to 4% by weight of the dopamine gel formulation.

3. The dopamine gel formulation according to claim 1, wherein said castor oil is present in the dopamine gel formulation in an amount of from 85% to 95% by weight of the dopamine gel formulation.

4. The dopamine gel formulation according to claim 1, wherein said oleoyl macrogolglyceride or a mixture of oleoyl macrogolglycerides is present in an amount of from 1% to 20% by weight of the dopamine gel formulation.

5. The dopamine gel formulation according to claim 1, further comprising at least one surfactant selected from the group consisting of lecithin, a fatty acid ester, at least one humectant, and mixtures thereof.

6. The dopamine gel formulation according to claim 1, wherein said colloidal silicon dioxide is present in an amount of from 2% to 5% by weight of the dopamine gel formulation.

7. The dopamine gel formulation according to claim 1, further comprising a thickener or gelling agent selected from the group consisting of cellulose, cellulose derivatives, polysaccharides, carbomers, polyvinyl alcohol, povidone, colloidal silicon dioxide, cetyl alcohols, stearic acid, beeswax, petrolatum, triglycerides, lanolin and mixtures thereof.

8. The dopamine gel formulation according to claim 1, wherein said dopamine is in the form of microspheres.

9. The dopamine gel formulation according to claim 1, wherein said dopamine is in the form of liposomes.

10. A dopamine gel formulation comprising: (a) dopamine in an amount of about 2% by weight of the formulation; (b) castor oil in an amount of about 90% by weight of the formulation; (c) an oleoyl macrogolglyceride or a mixture of oleoyl macrogolglycerides in an amount of about 4% by weight of the formulation; and (d) colloidal silicon dioxide in an amount of about 4% by weight of the formulation.

\* \* \* \* \*